United States Patent [19]

Nakane

[11] Patent Number: 4,652,576
[45] Date of Patent: Mar. 24, 1987

[54] 7-OXABICYCLOHEPTANE SUBSTITUTED AMIDE-CARBAMATE PROSTAGLANDIN ANALOGS

[75] Inventor: Masami Nakane, Hopewell, N.J.

[73] Assignee: E. R. Squibb & Sons, Inc., Princeton, N.J.

[21] Appl. No.: 789,273

[22] Filed: Oct. 18, 1985

[51] Int. Cl.$^4$ ............... C07D 493/08; C07D 405/14; A61K 31/34; A61K 31/41

[52] U.S. Cl. .................. 514/382; 514/469; 548/252; 549/463

[58] Field of Search ............ 549/463; 548/252; 514/382, 469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,617 | 6/1984 | Nakane et al. | 424/285 |
| 4,526,901 | 7/1985 | Nakane | 514/469 |

FOREIGN PATENT DOCUMENTS 0043292 8/1982 European Pat. Off. .
2039909 8/1980 United Kingdom .

Primary Examiner—Robert Gerstl
Attorney, Agent, or Firm—Lawrence S. Levinson; Burton Rodney

[57] ABSTRACT

7-Oxabicycloheptane substituted amide-carbamide prostaglandin analogs are provided having the structural formula

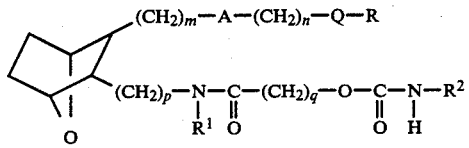

wherein m is 0 to 4; A is —CH=CH— or —CH$_2$—CH$_2$—; n is 1 to 5; Q is —CH=CH—, —CH$_2$—,

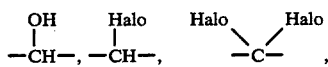

or a single bond; R is $CO_2H$, $CO_2$alkyl, $CO_2$alkali metal, $CO_2$polyhydroxyamine salt, —CH$_2$OH,

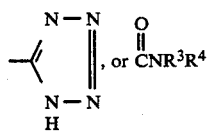

wherein $R^3$ and $R^4$ are the same or different and are H, lower alkyl, hydroxy, lower alkoxy or aryl, at least one of $R^3$ and $R^4$ being other than hydroxy and lower alkoxy; p is 1 to 5; $R^1$ is H or lower alkyl; q is 1 to 12; and $R^2$ is H, lower alkyl, lower alkenyl, lower alkynyl, aryl, or arylalkyl.

The compounds are cardiovascular agents useful, for example, in the treatment of thrombotic disease.

16 Claims, No Drawings

7-OXABICYCLOHEPTANE SUBSTITUTED AMIDE-CARBAMATE PROSTAGLANDIN ANALOGS

DESCRIPTION OF THE INVENTION

The present invention relates to 7-oxabicycloheptane substituted amide-carbamate prostaglandin analogs which are cardiovascular agents useful, for example, in the treatment of thrombotic disease. These compounds have the structural formula

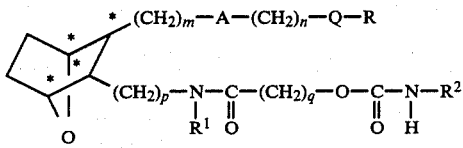

including all stereoisomers thereof, wherein m is 0 to 4; A is —CH=CH— or —$CH_2$—$CH_2$—; n is 1 to 5; Q is —CH=CH—, —$CH_2$—,

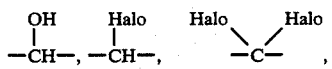

or a single bond; R is $CO_2H$, $CO_2$ alkyl, $CO_2$ alkali metal, $CO_2$ polyhydroxyamine salt, —$CH_2OH$,

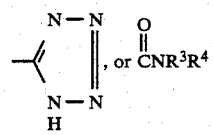

wherein $R^3$ and $R^4$ are the same or different and are H, lower alkyl, hydroxy, lower alkoxy or aryl at least one of $R^3$ and $R^4$ being other than hydroxy and lower alkoxy; p is 1 to 5; $R^1$ is H or lower alkyl; q is 1 to 12; and $R^2$ is H, lower alkyl, lower alkenyl, lower alkynyl, aryl, or arylalkyl.

The term "lower alkyl" or "alkyl" as employed herein alone or as part of another group includes both straight and branched chain hydrocarbon radicals of from 1 to 12 carbons, such as methyl, ethyl, propyl isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent, or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups 1 or 2 lower alkoxy groups. 1 or 2 hydroxy groups, 1 or 2 alkylamino groups, 1 or 2 alkanoylamino groups, 1 or 2 arylcarbonylamino groups 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms $(CH_2)_m$, $(CH_2)_n$ and $(CH_2)_p$ includes straight or branched chain radicals having from 0 to 4 carbons in the normal chain in the case of $(CH_2)_m$, from 1 to 5 carbons in the normal chain in the case of $(CH_2)_n$ and from 1 to 5 carbons in the normal chain in the case of $(CH_2)_p$ and may contain one or more lower alkyl and/or halogen substituents. Examples of $(CH_2)_m$, $(CH_2)_n$ and $(CH_2)_p$ groups include $CH_2$,

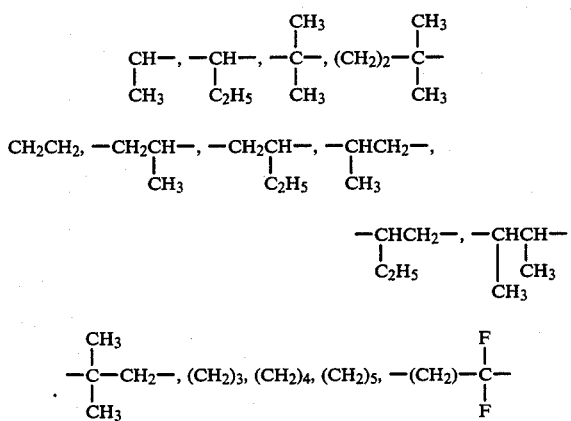

-continued

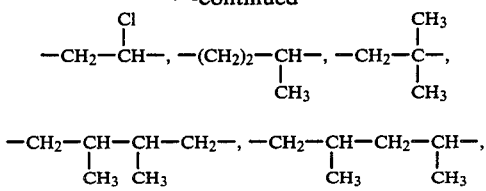

and the like.

The term $(CH_2)_q$ includes straight or branched chain radicals having from 1 to 12 carbons in the normal chain and includes any of the above examples of $(CH_2)_m$, $(CH_2)_n$ and $(CH_2)_p$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

wherein $R^5$ and $R^6$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein m is 1 or 2, A is a —CH=CH—, n is 1 or 4, Q is a single bond or —C(F$_2$)—,

$(CH_2)_2$, or —CH=CH, R is $CO_2H$ or $CH_2OH$; p is 1, $R^1$ is H, $(CH_2)_q$ is —CH$_2$—; and $R^2$ is lower alkyl, such as pentyl, hexyl, or heptyl.

The compounds of formula I of the invention may be prepared as described below.

A. p is 1, m is 1, Q is —CH$_2$— or a single bond and $R^1$ is H

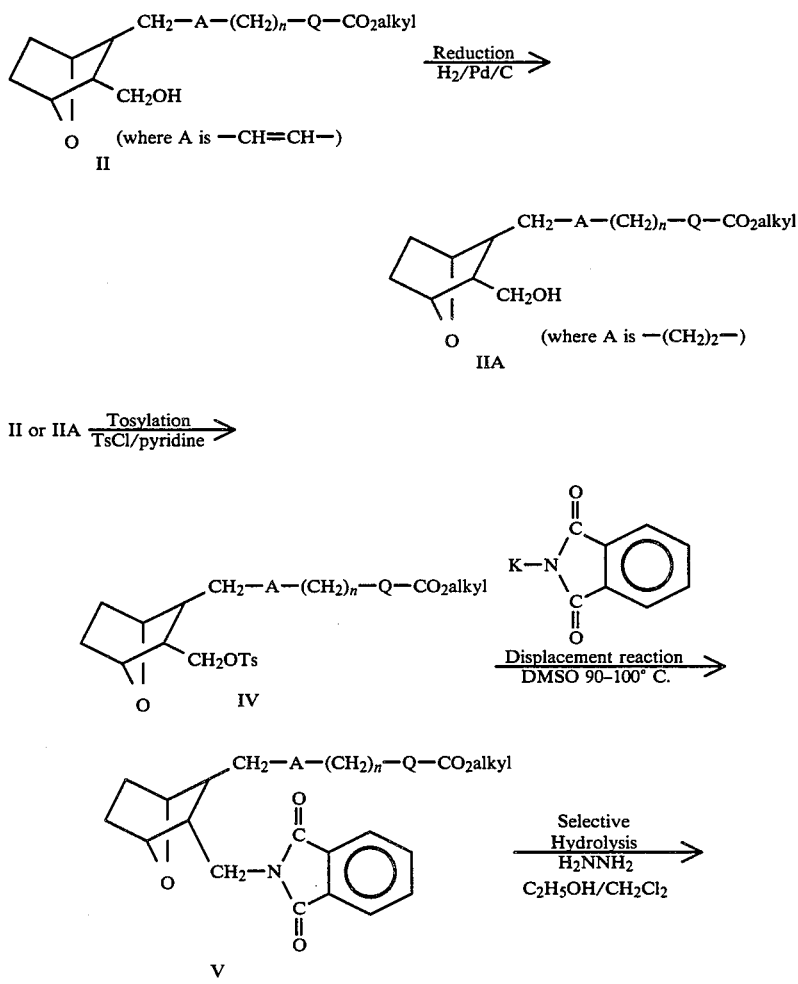

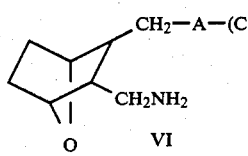 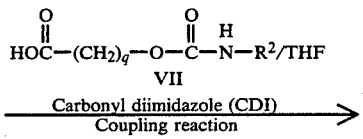
-continued
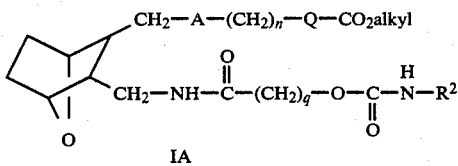
A'. Where p is 1, m is 1, Q is —CH$_2$— or a single bond and R$^1$ is alkyl
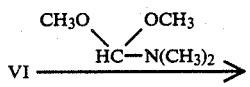
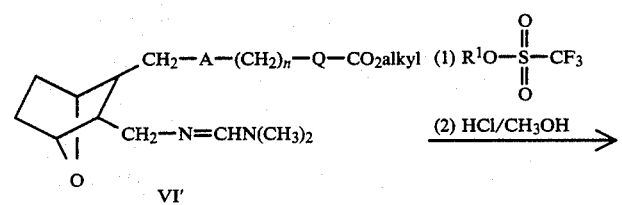
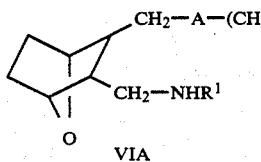 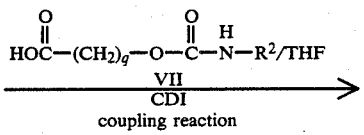
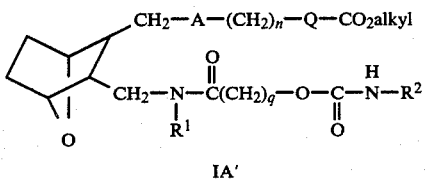
B. Where Q is CH$_2$ or a single bond, p is 2 to 5, m is 1 and R$^1$ is H
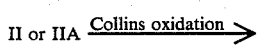
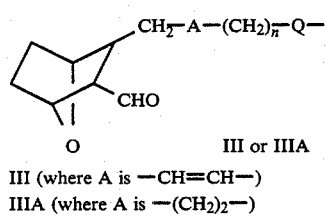
III (where A is —CH=CH—)
IIIA (where A is —(CH$_2$)$_2$—)
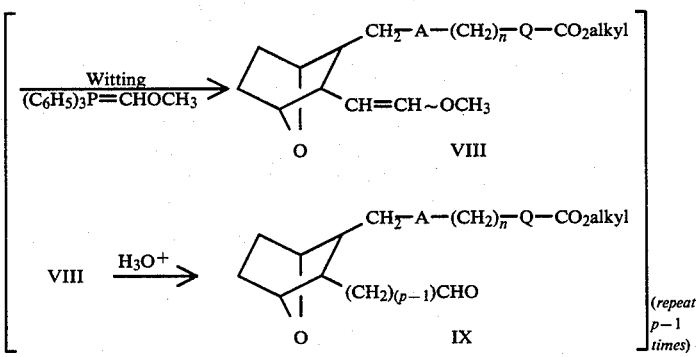
(repeat p−1 times)

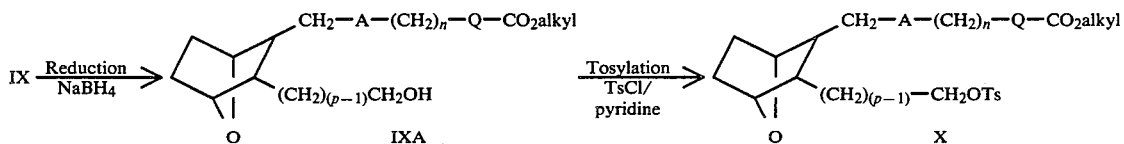
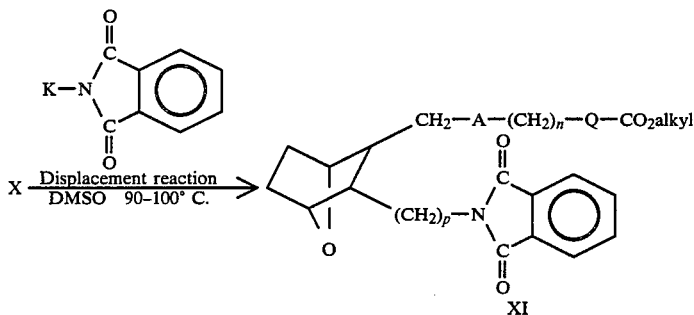
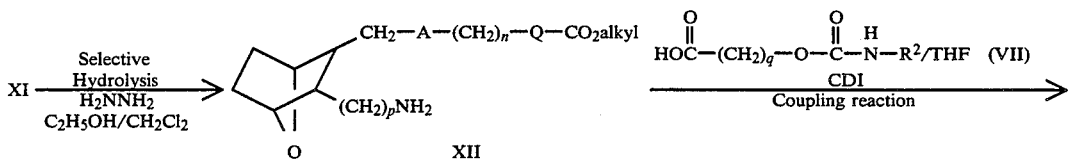
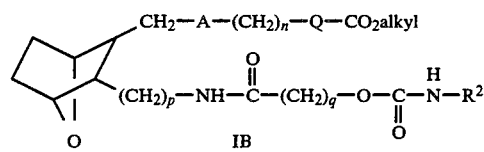
B'. Where Q is $CH_2$ or a single bond, p is 2 to 5, m is 1 and $R^1$ is alkyl
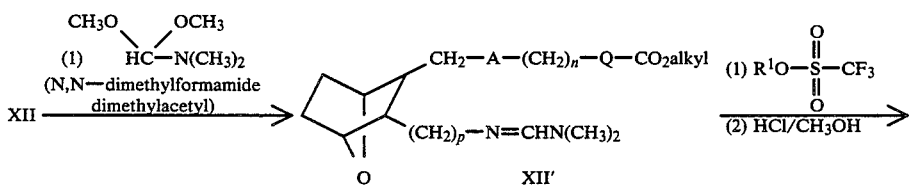
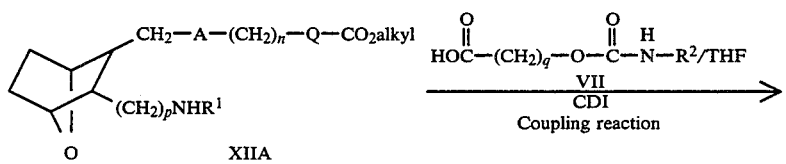
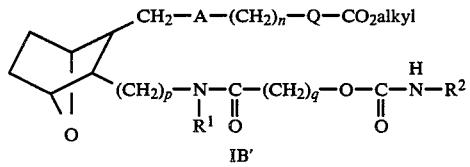
C. Where m is 2, p is 1, A is —CH=CH— and Q is $CH_2$ or a single bond
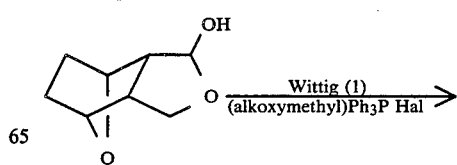

-continued

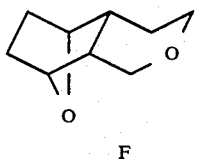
F

E. Where m is 3 or 4, p is 1, A is —CH=CH— and Q is $CH_2$ or a single bond

XIV $\xrightarrow[\text{m is 4}]{\text{Repeat Wittig (1)}\\\text{1 time if m is 3}\\\text{and 2 times if}}$

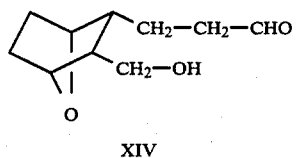
XIV

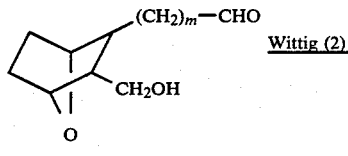
XVII

XIV $\xrightarrow[\text{Carboxyalkyl}Ph_3P\text{ Hal}]{\text{Wittig (2)}}$

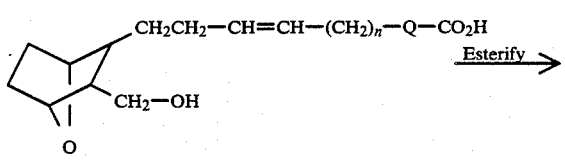
XV

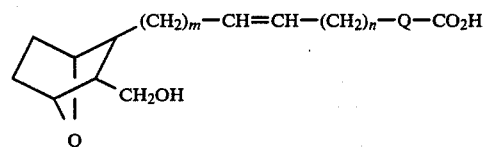
XVIII

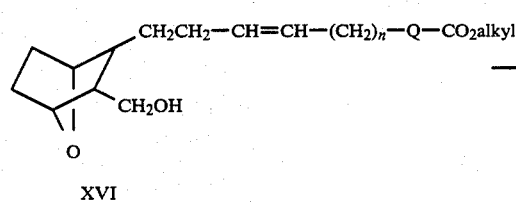
XVI

XVIII $\xrightarrow{\text{Esterification}}$

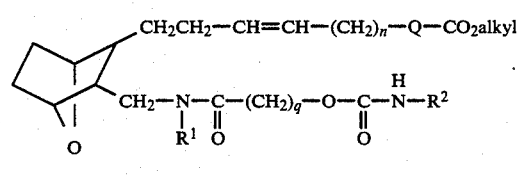
XVI

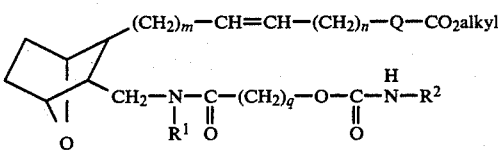
XIX

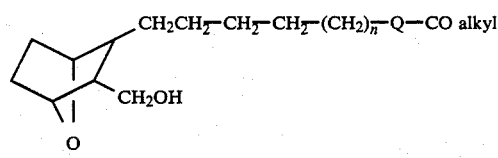
IC

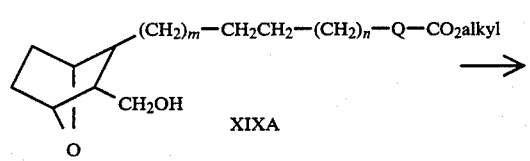
IE

D. m is 2, p is 1, A is —$CH_2$—$CH_2$— and Q is $CH_2$ or a single bond

F. Where m is 3 or 4, p is 1, A is $CH_2CH_2$ and Q is $CH_2$ or a single bond

XVI $\xrightarrow{\text{Reduction}\\H_2/Pd/C}$

XIX $\xrightarrow{\text{Reduction}\\H_2/Pd/C}$

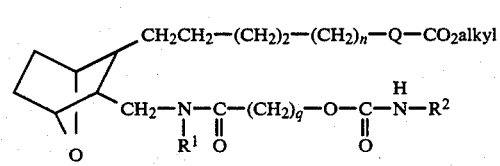
XVIA

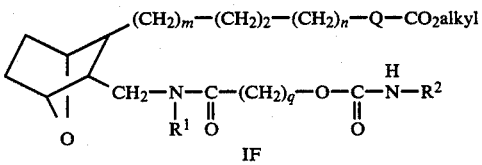
XIXA

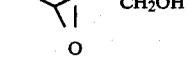
ID

IF

G. Where m=0, A is —CH=CH—, p is 1, Q is $CH_2$ or a single bond

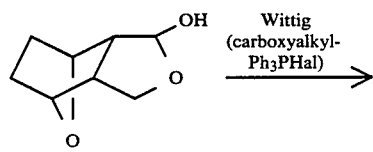

XIII

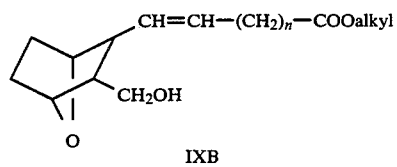

IXB

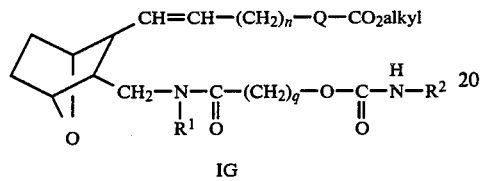

IG

H. Where m=0, A is —(CH$_2$)$_2$—, p is 1, Q is CH$_2$ or a single bond

IXB $\xrightarrow{\text{Reduction}}{\text{H}_2\text{/Pd/C}}$

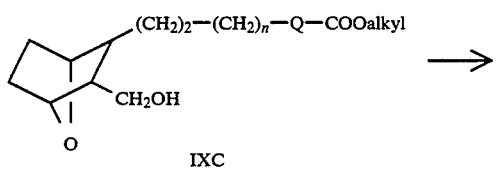

IXC

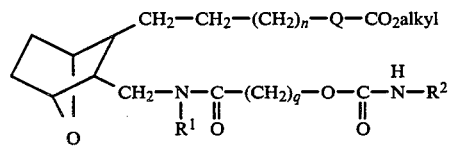

IH

I. Where Q is —CH=CH—

IA,
IB,
IC,
IE,
IG $\xrightarrow[\text{O}_3]{\text{Ozonolysis}}$

[structure XX with (CH$_2$)$_m$—CHO and (CH$_2$)$_p$—N(R$^1$)—C(O)—(CH$_2$)$_q$—O—C(O)—N(H)—R$^2$] $\xrightarrow[\text{(C}_6\text{H}_5)_3\text{P}=\text{CH}-(\text{CH}_2)_n-\text{CH}=\text{CH}-\text{CO}_2\text{H}]{\text{Wittig}}$ (where A is CH=CH)

[structure IJ with (CH$_2$)$_m$—A—(CH$_2$)$_n$—CH=CH—CO$_2$H and (CH$_2$)$_p$—N(R$^1$)—C(O)—(CH$_2$)$_q$—O—C(O)—N(H)—R$^2$]

IJ

J. Where Q is halo halo halo
—CH— or —C— XX $\xrightarrow[(\text{C}_6\text{H}_5)_3\text{P}=\text{CH}-(\text{CH}_2)_n-\overset{(\text{halo})_x}{\text{C}}-\text{CO}_2^{\ominus}]{\text{Wittig}}$
(where A is CH=CH and x is 1 or 2)

[structure IK with (CH$_2$)$_m$—A—(CH$_2$)$_n$—C(halo)$_x$—CO$_2$H and (CH$_2$)$_p$—N(R$^1$)—C(O)—(CH$_2$)$_q$—O—C(O)—N(H)—R$^2$]

IK

K. Where Q is

IA,
IB,
IC,
OH  ID, (1) LiN(i-C$_3$H$_7$)$_2$
—CH— IE, (2) MoO$_5$PyHMPA $\longrightarrow$
IF,
IG,
IH

[structure IL with (CH$_2$)$_m$—A—(CH$_2$)$_n$—CH(OH)—CO$_2$alkyl and (CH$_2$)$_p$—N(R$^1$)—C(O)—(CH$_2$)$_q$—O—C(O)—N(H)—R$^2$]

IL

L. Where R is $\overset{\text{O}}{\underset{}{\|}}$
CNR$^3$R$^4$ (wherein R$^3$ and R$^4$ are other than hydroxy or alkoxy)

IA,
IB,
IC,
ID,
IE,      HNR³R⁴ →
IF,
IG,
IH,
or IL
or esters of
IJ or IK

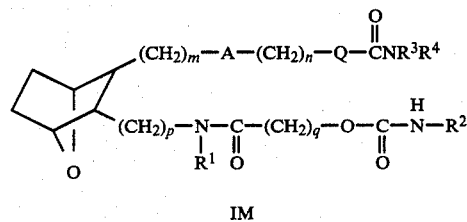

IM

M. Where R is

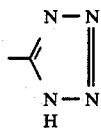

and A is CH=CH

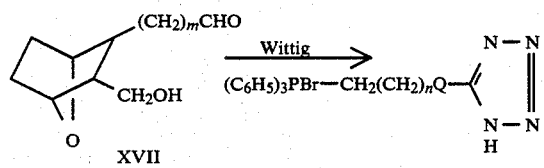

XVII    Wittig
        (C₆H₅)₃PBr—CH₂(CH₂)ₙQ

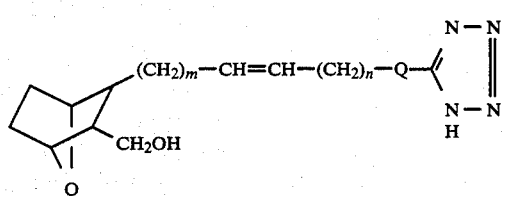

IIC

IIC →

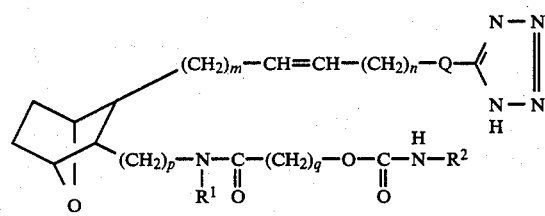

IN

N. Where R is <image from formula> and A is (CH₂)₂

IN  Reduction →
    H₂/Pd/C

-continued

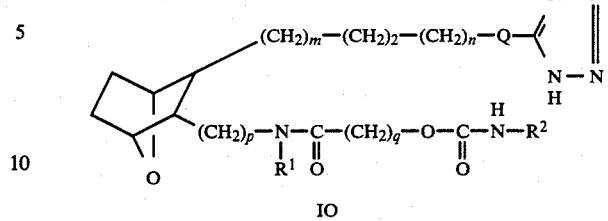

IO

O. Where R is CH₂OH

IA to IH,   NaBH₄
IL,            or
or          LiBH₄  →
esters of
IJ and IK

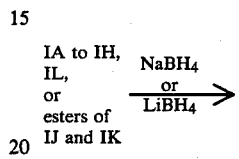

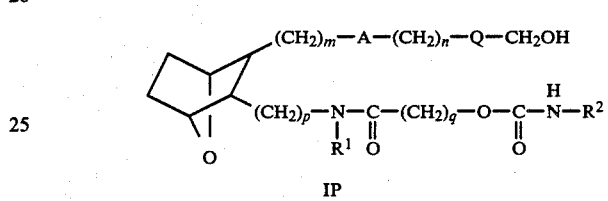

IP

P. Where R is CO₂H hydrolysis
IA to IH, IL  LiOH, HCl →

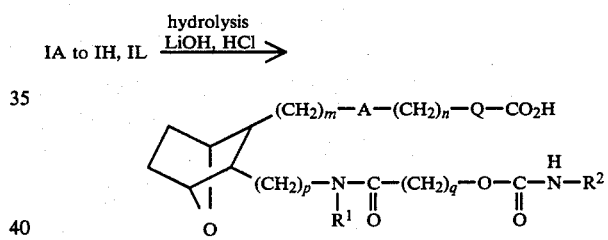

(IQ where A is CH=CH)
(IR where A is (CH₂)₂)
Q. Where R is

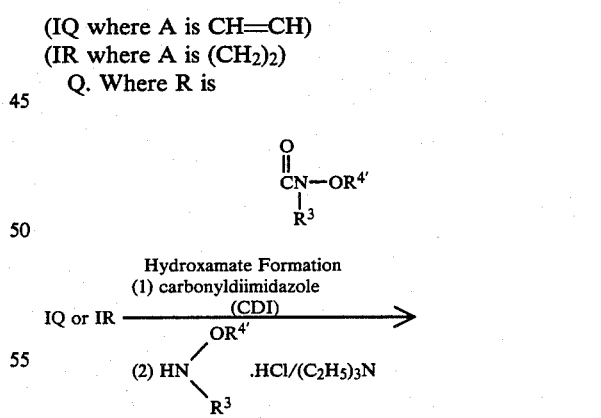

IQ or IR  Hydroxamate Formation
          (1) carbonyldiimidazole
                    (CDI)

(2) HN(OR⁴')(R³) · HCl/(C₂H₅)₃N
                               →

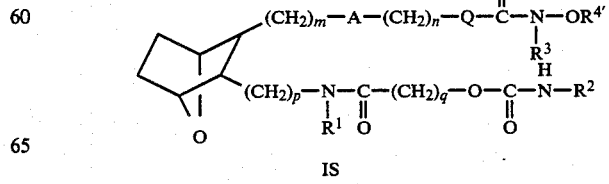

IS (wherein R⁴' is H or alkyl)

As seen in reaction sequence "A", compounds of the invention where Q is —CH₂— or a single bond, p is 1, R is CO₂ alkyl, and R¹ is H, that is

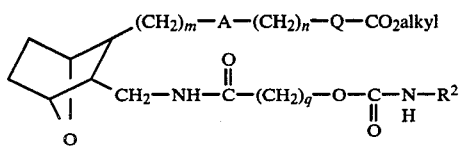

are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

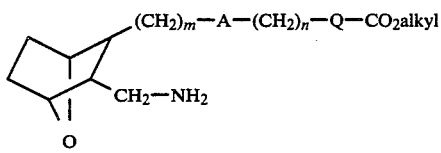

As seen in reaction sequence "A'", where R¹ is lower alkyl, an alkylation reaction is carried out as in the reference M. J. O'Donnell et al., *Tetrahedron Lett.* (1984), 25, 3651–3654 to give VIA

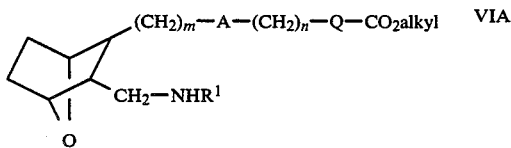

The amine VI or VIA is then subjected to a CDI coupling reaction by reacting VI or VIA with acid VII

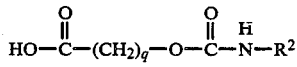

in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound of the invention IA or IA'

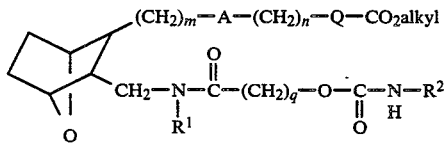

(IA—where R¹ is H
IA'—where R¹ is lower alkyl)

The reaction sequences identified as "B" and "B'" are employed to prepare compounds of the invention wherein Q is —CH₂— or a single bond, p is 2 to 5, and R is CO₂alkyl, that is,

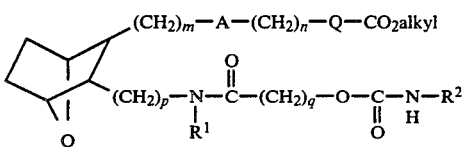

(IB—where R¹ is H
IB'—where R¹ is alkyl)

Compound II or IIA is used to form the aldehyde III (where A is —CH=CH—) or IIIA (where A is —(CH₂)₂). Thus, to form aldehyde III where A is —CH=CH—, comound II is subjected to a Collins oxidation, for example, by reacting II with chromium trioxide in pyridine. To form the aldehyde IIIA (where A is (CH₂)₂) compound II is reduced, for example, with hydrogen over a palladium on carbon catalyst, to form hydroxymethyl compound IIA (where A is (CH₂)₂) and compound IIA is subjected to a Collins oxidation to form aldehyde IIIA (where A is (CH₂)₂). The aldehyde III or IIIA is used to prepare aldehyde IX (where p is 2–5) by carrying out a homologation sequence, such as a Wittig reaction with (C₆H₅)₃P=CHOMe followed by hydrolysis, (p-1) times. The aldehyde IX (where p is 2–5) is then carried on to compounds of this invention where p is 2–5, that is

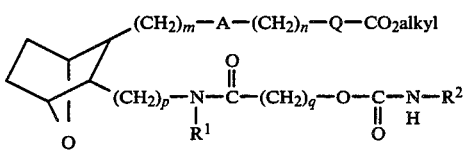

(where p is 2 to 5) by reducing aldehyde IX by reacting with a reducing agent such as sodium borohydride to form alcohol IXA

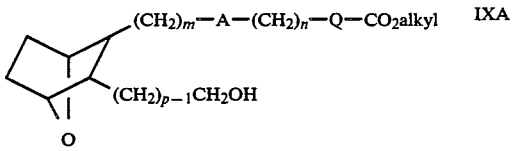

tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

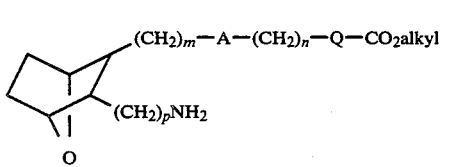

As seen in reaction sequence "B'", where R¹ is lower alkyl, an alkylation reaction is carried out as in O'Donnell et al, supra to give XIIA

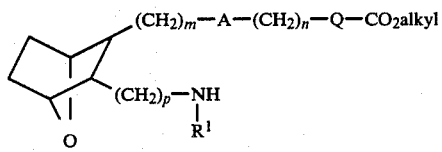

The amine XII or XIIA is then reacted with acid VII in a CDI coupling reaction as described above to form the amide ester compound of the invention IB or IB'

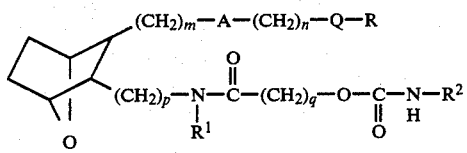

(IB—where $R^1$ is H
IB'—where $R^1$ is lower alkyl)

Compounds of the invention wherein m is 2, A is —CH=CH—, p is 1 and Q is $CH_2$ or a single bond may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound F. The Wittig (1) procedure is repeated on compound F to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —$CH_2$—$CH_2$—, p is 1 and Q is $CH_2$ or a single bond may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH=CH—, p is 1 and Q is $CH_2$ or a single bond may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is $CH_2CH_2$, p is 1 and Q is $CH_2$ or a single bond may be prepared by reducing hydroxymethyl compound XIX to form compound XIXA which is then employed in place of compound II in reaction scheme "A" to form compound IF of the invention.

Thus, compounds of the invention wherein mm is 0, 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

Referring now to reaction sequence "G", compounds of the invention wherein m is 0, A is CH=CH, p is 1 and Q is $CH_2$ or a single bond, that is, compound IG may be prepared by subjecting compound XIII (prepared as described in Example 3 of U.S. Pat. No. 4,143,054) to a Wittig reaction, for example, as described in Example 6(c) of U.S. Pat. No. 4,143,054, by reacting XIII with a carboxyalkyltriphenyl phosphonium halide, such as carboxypentyltriphenyl phosphonium bromide to form the hydroxymethyl compound IXB which may then be used to form the ester IG which, in turn, may be hydrolyzed to the corresponding acid.

As seen in reaction sequence "H", where it is desired to prepare compounds of the invention wherein m is 0 and A is $(CH_2)_2$, the hydroxymethyl compound IXB is reduced by treatment with hydrogen in the presence of a palladium on carbon catalyst to form hydroxymethyl compound IXC which may then be used to form ester IH which then may be hydrolyzed to the corresponding acid.

Referring to reaction sequence "I", compounds of formula I of the invention wherein Q is —CH=CH—, that is IJ

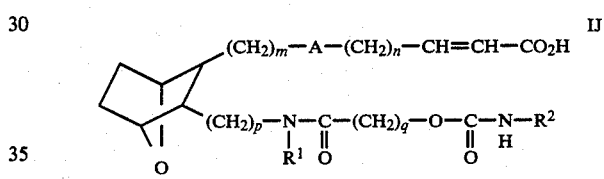

may be prepared by subjecting ester IA, IB, IA', IB', IC, IE and IG to ozonolysis by treating IA, IB, IA', IB', IC, IE and IG with ozone at −78° C. in methylene chloride and methanol to form aldehyde XX.

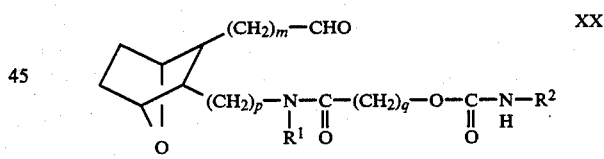

which is then treated with Wittig reagent

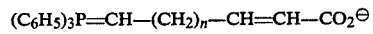

(where A is (—CH=CH—)) to form IJ.

In reaction sequence "J" compounds wherein Q is

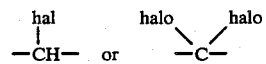

are prepared by subjecting aldehyde XX to a Wittig reaction with

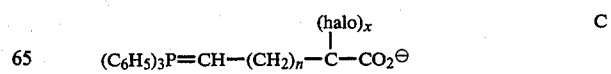

(where A is CH=CH and x is 1 or 2) to form compounds of the invention IK

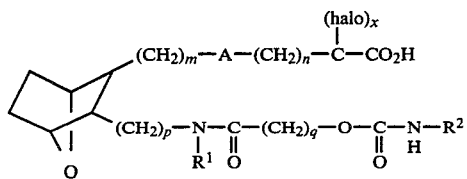

As seen in reaction sequence "K" compounds of the invention wherein Q is

that is, IL

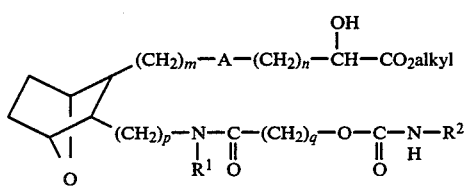

are formed by reacting ester IA to IH with lithium diisopropylamide in the presence of an inert solvent such as tetrahydrofuran at reduced temperatures of lower than about −50° C. and then with oxodiperoxymolybdenum(pyridine)(hexamethylphosphoric triamide) (MoO5PyHMPA).

In reaction sequence "L", amides of the invention of structure IM

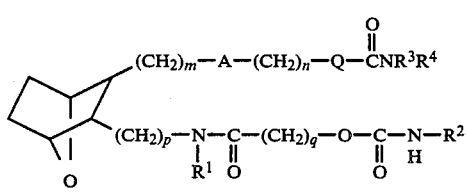

wherein $R^3$ and $R^4$ are independently H, alkyl or aryl are prepared by treating ester IA to IH or IL or esters of IJ or IK with an amine of the structure

HNR$^3$R$^4$.  E

Compounds of the invention wherein R is tetrazole

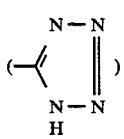

and A is CH=CH are prepared as described in reaction sequence "M" wherein alcohol XVII

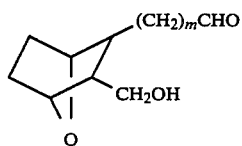

(prepared as described in U.S. Pat. No. 4,143,054) is reacted with a Wittig reagent of the structure G

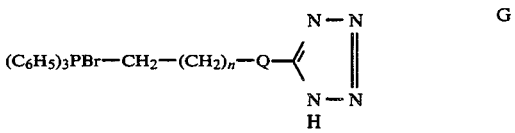

in the presence of a base, such as potassium t-butoxide or sodium hydride-dimethyl sulfoxide employing a molar ratio of F:G of within the range of from about 1:1 to about 0.2:1 to form the hydroxymethyl compound IIC

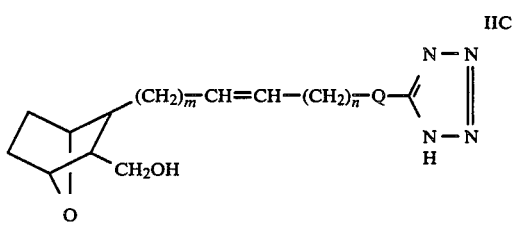

which may then be employed in reaction sequences "A" and "B" in place of compounds II or IIA to form compounds of the invention IN where A is —CH=CH— or IO where A is (CH$_2$)$_2$

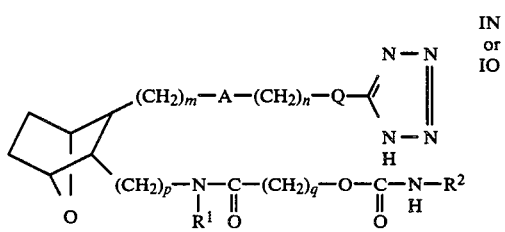

Alternatively, compound IO may be prepared by reducing compound IN by treating with H$_2$ in the presence of palladium on charcoal.

Compounds of the invention wherein R is tetrazole and A is CH=CH may also be prepared by reacting aldehyde XX in the reaction sequence "I" with a Wittig reagent of the structure G in the presence of base such as potassium t-butoxide or sodium hydride-dimethyl sulfoxide as described above.

As seen in reaction sequence "O", compounds of the invention wherein R is CH$_2$OH may be prepared by reducing esters IA to IH, and IL and esters of J and K by treatment with sodium borohydride or lithium borohydride to form compounds of the invention IP

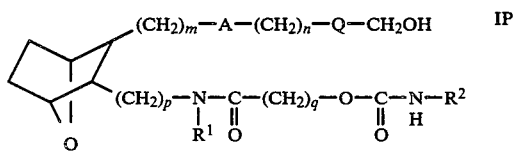

Referring to reaction sequence "P", the esters IA, IA', IB, IB' to IH and IL can be converted to the free acid, that is, to

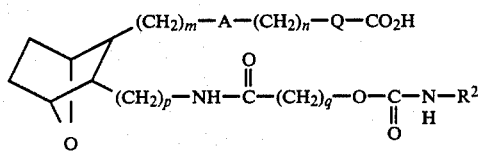

IQ (A is —CH=CH—)
IR (A is (CH$_2$)$_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IQ and IR.

In the reaction sequence identified as "Q" where in Formula I,

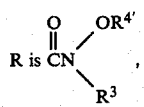

wherein R$^{4'}$ is H or alkyl, a solution of acid dissolved in an inert organic solvent such as tetrahydrofuran is treated with carbonyl diimidazole and the mixture is stirred at room temperature under nitrogen. The resulting solution is added dropwise into a cold solution of amine hydrochloride H

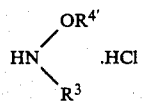

(wherein R$^{4'}$ is H or alkyl, employing a molar ratio of acid chloride:H of within the range of from about 0.3:1 to about 1:1 and preferably from about 0.5:1) and triethylamine in tetrahydrofuran to form the hydroxamate IS.

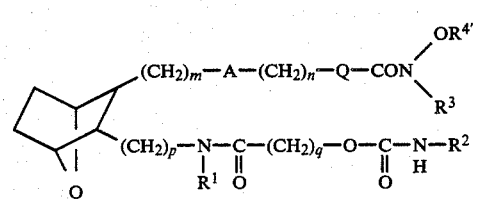

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The starting acid VII

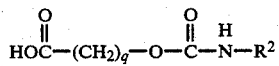

may be prepared by reacting the ester-alcohol J

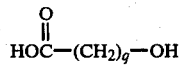

with isocyanate K

O=C=N—R$^2$    K in the presence of an organic base such as triethylamine to form L

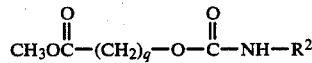

Compound L is treated with strong base such as sodium hydroxide and water to form VII.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

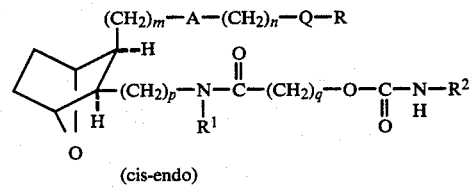
(cis-endo)

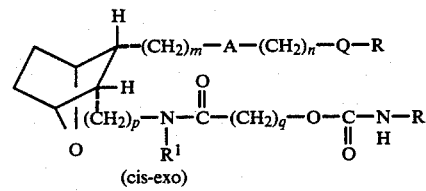
(cis-exo)

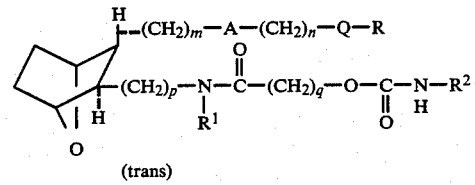
(trans)

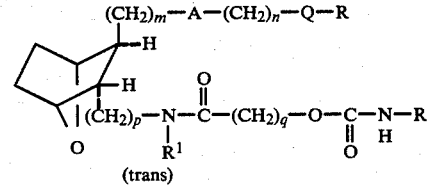
(trans)

The nucleus in each of the compounds of the invention is depicted as

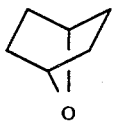

for matter of convenience; it will also be appreciated that the nucleus in the compounds of the invention may be depicted as

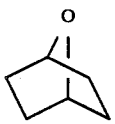

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 0.1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1β,2α(5Z),3α,4β]]-7-[3-[[[[(Butylamino)carbonyl]oxy]acetyl]amino]methyl]-7-oxabicyclo-[2.2.1]hept-2-yl]-5-heptenoic acid, methyl ester A. [[(Butylamino)carbonyl]oxy]acetic acid (1) [[(Butylamino)carbonyl]oxy]acetic acid, methyl ester Methyl glycolate (1.8 g, 20 mmol) was cooled in an ice bath. Triethylamine (180 μl, ~1.3 mmol) was added followed by n-butyl isocyanate (2.92 ml, 26 mmol). The mixture was stirred cold for 30 minutes and then overnight at room temperature. The triethylamine was removed in vacuo and the crude product was purified on a silica gel column (60 g, Baker for flash chromatography) eluting with 30% ether in petroleum ether to give 3.76 g of pure title ester (99%).

(2) [[(Butylamino)carbonyl]oxy]acetic acid

The ester oil from Part (1) (1.82 g, 9.6 mmol) was treated with 2N NaOH (20 ml). The heterogeneous mixture was stirred vigorously at room temperature and became homogeneous in about 30 minutes. After stirring 4 hours, the reaction was washed with ether (2×30 ml) and the ether washes were reextracted with 2N NaOH solution (10 ml). The combined aqueous layers were acidified to pH 1 with concentrated HCl and the product was extracted into ether (2×30 ml). The combined ether extracts were washed with saturated NaCl solution (2×20 ml), dried ($MgSO_4$) and freed of solvent in vacuo. The crude solid obtained (1.48 g) was recrystallized from benzene to give title acid (1.11 g, 6.3 mmol, 66%) as colorless crystals, m.p. 83°–84°.

B. [1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in $CH_2Cl_2$ (30 ml) was added dropwise to a magnetically stirred solution of [1S-[1β,2α(5Z),3α,4β]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/$H_2O$ and stirred for 30 minutes. The products were extracted with EtOAc (80 ml×3). The combined EtOAc layers were washed with 3N-HCl (40 ml×3), saturated $NaHCO_3$, brine and dried over $MgSO_4$. Filtration and evaporation of solvent gave a white solid, which was crystallized from isopropyl ether to give the corresponding title tosylate in the form of needle crystals (4.23 g, 89%), m.p. 68°–70° C.

C. [1S-[1β,2α(5Z),3α,4β]]-7-[(3-(Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°–100° C. for 2½ hours (checked by TLC $Et_2O$-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO$_4$), filtered and freed of solvent in vacuo. The remaining solid (7.88 g) was recrystallized from isopropyl ether (~150 ml) to give corresponding phthalimide (6.35 g, 83%) TLC. Et$_2$O-hexane 2:1, UV+vanillin R$_f$=0.38, trace 0.09.

The above phthalimide (5.05 g, 13.8 mmol) was dissolved in distilled CH$_2$Cl$_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more CH$_2$Cl$_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid K$_2$CO$_3$. The amine was extracted into CHCl$_3$ (3×100 ml), dried (MgSO$_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D.

[1S-[1β,2α(5Z),3α,4β]]-7-[3-[[[[[(Butylamino)carbonyl]oxo]acetyl]amino]methyl]-7-oxabicyclo[2.2.1]hept-2-yl]-5-heptenoic acid, methyl ester Part A compound (262.5 mg, 1.5 mmol) was dissolved in distilled THF (12 ml) in an argon atmosphere. After cooling in an ice bath carbonyldiimidazole (CDI) (243.2 mg, 1.5 mmol) was added. The mixture was stirred cold for 1 hour and then at room temperature for 1 hour. The solution was cooled to 0° C. and a solution of Part C amine (401 mg, 1.5 mmol) in THF (3 ml) was added. The mixture was left stirring overnight at room temperature. The solvent was removed in vacuo and the residue was dissolved in CHCl$_3$ (50 ml). This was washed with 1N HCl (20 ml), 1N NaOH (20 ml) and H$_2$O (20 ml), dried (MgSO$_4$) and freed of solvent in vacuo leaving a viscous oil. The oil was chromatographed on silica gel (25 g, Baker for flash chromatography), eluting with 2% MeOH in ether to give title compound as an oil (230 mg, 54%). TLC: silica gel, 5% MeOH in ether, vanillin R$_f$=0.45.

EXAMPLE 2

[1S-[1β,2α,(5Z),3α,4β]]-7-[3-[[[[[(Butylamino)carbonyl]oxy]acetyl]amino]methyl]-7-oxabicyclo[2.2.1]hept-2-yl]-5-heptenoic acid The Example 1 methyl ester (227 mg, 0.535 mmol) was dissolved in distilled THF (40 ml) and water (8 ml) in an argon atmosphere. 1N LiOH solution (9.5 ml) was added and the mixture was stirred at room temperature for 80 minutes. After neutralization with 1N HCl (9.5 ml), solid KCl was added and the layers were separated. The aqueous layer was reextracted with CHCl$_3$ (3×50 ml). The combined organic layers (THF+CHCl$_3$) were washed with saturated NaCl solution (2×25 ml), dried (MgSO$_4$), and freed of solvent in vacuo leaving an oil. This was chromatographed on silica gel (20 g, Baker for flash chromatograhy), eluting with 4% MeOH in CH$_2$Cl$_2$ to give title acid in the form of an oil (160 mg, 72%). TLC: silica gel, 10% MeOH in CH$_2$Cl$_2$, vanillin, R$_f$=0.41.

Anal Calcd for C$_{21}$H$_{34}$O$_6$N$_2$.0.25H$_2$O: C, 60.77; H, 8.38; N, 6.75, Found: C, 60.81; H, 8.43; N, 6.64.

EXAMPLE 3

[1S-[1β,2α(5Z),3α,4β]]-2,2-Difluoro-7-[3-[[[[[(Butylamino)carbonyl]oxy]acetyl]amino]methyl]-7-oxabicyclo[2.2.1]hept-2-yl]-5-heptenoic acid

A.

[1S-[1β,2α,3α,4β]]-2-[3-[[[[(butylamino)carbonyl]oxy]acetyl]amino]methyl]-7-oxabicyclo[2.2.1]-hept-2-yl]acetaldehyde O$_3$ is bubbled through a magnetically stirred solution of [1S-[1β,2α(5Z),3α,4β]]-7-[3-[[[[(butylamino)carbonyl]oxy]acetyl]amino]methyl]-7-oxabicyclo[2.2.1-]hept-2-yl]-5-heptenoic acid, methyl ester (212.2 mg, 0.5 mmol) (prepared as described in Example 1) in CH$_2$Cl$_2$/MeOH (10 ml/10 ml) at −78° C., until the solution becomes blue. Excess O$_3$ is then purged by a stream of N$_2$ and (CH$_3$)$_2$S (1 ml) is added. The reaction is allowed to warm to room temperature and poured into CH$_2$Cl$_2$ (50 ml), H$_2$O (10 ml). The products are extracted into CH$_2$Cl$_2$ layers. The H$_2$O layer separated is re-extracted with CH$_2$Cl$_2$ (30 ml). The combined CH$_2$Cl$_2$ layers are washed with brine (10 ml) and dried over MgSO$_4$. Filtration and evaporation of solvent gives a crude product which is purified by silica gel column chromatography to afford the title compound.

B. (4-Carboxy-3,3-difluorobutyl)triphenylphosphonium bromide

(1) Methyl tetrahydrofuroate

Methyl furoate (75 g, 0.595 mole) was dissolved in MeOH (150 ml), and poured into a Parr bottle. Air was replaced with argon, and then 10% Pd/C (2.5 g) was added. The atmosphere was replaced with H$_2$ and methyl furoate was hydrogenated at 40 psi for 48 hours. The reaction was filtered through celite pad, and the pad was washed with ether. The filtrate and the wash were combined and distilled to give the title compound (71 g, 0.546 mole, 59° C./5.1 mmHg, 92%) as a colorless liquid.

(2) Methyl 2-acetoxy-5-bromopentanoate

HBr gas was bubbled into Ac$_2$O (200 ml) at 0° C. for 2 hours. The specific gravity became 1.4. Part 1) methyl tetrahydrofuroate (70 g, 0.538 mole) was added dropwise under magnetic stirring at 0° C. and the reaction was allowed to warm to room temperature. After stirring overnight, the reaction was poured into ice (~1200 ml) carefully, and left for 30 minutes with occasional swirling. The products were extracted with Et$_2$O (600 ml×2 and 300 ml). The combined Et$_2$O layers were washed with dilute NaOH (~0.5%) solution, until the wash became basic. The Et$_2$O layer was further washed with H$_2$O, dried over Na$_2$SO$_4$, and filtered. The filtrate was concentrated and distilled to give the title compound (116 g, 0.458 mole, 108° C./1 mm Hg, 85%) as a colorless liquid.

(3) Methyl 5-bromo-2-hydroxypentanoate

MeOH (100 ml, distilled over Mg(OMe)$_2$) was saturated with HBr gas at 0° C. This was added to Part 2) compound (60 g, 0.237 mole) in MeOH (200 ml distilled over Mg(OMe)$_2$). The reaction was allowed to warm to room temperature and stirred overnight. The reaction was concentrated in vacuo. Toluene (200 ml) was added to the resulting liquid, and the reaction was concentrated. The same process was repeated twice. The resulting liquid was dissolved in EtOAc (2000 ml) and washed with 0.5% NaOH, brine, and dried over $MgSO_4$. Filtration and evaporation of solvent gave a straw colored oil (44.8 g). This was distilled to give the title compound (34 g, 0.161 mole, 68%) as a colorless liquid.

(4) Methyl 5-bromo-2-oxopentanoate

Jones' reagent ($CrO_3$: 9.58 g, $H_2SO_4$: 8.47 ml, $H_2O$: 36.8 ml) was added to a magnetically stirred solution of Part 3) compound (12.53 g, 59.3 mmole) in acetone (150 ml) at room temperature. The addition was controlled to maintain the temperature below 35° C. After the completion of the addition, the reaction was stirred at room temperature for 45 minutes. Isopropyl alcohol (30 ml) was added dropwise and stirred for 30 minutes. The reaction was then diluted with $H_2O$ (500 ml) and the products were extracted with $CH_2Cl_2$ (1 l.). The $CH_2Cl_2$ layer was washed with brine (100 ml×3) and dried over $MgSO_4$. Filtration and evaporation of solvents gave the title compound (11.4 g, 54.5 mmole, 92%) as a colorless liquid.

(5) Methyl 5-bromo-2,2-difluoropentanoate

Part (4) compound (11.4 g, 54.5 mmole) was added dropwise to $(C_2H_5)_2 NSF_3$ (DAST) (6.8 ml, 55.7 mmole) at room temperature. The container of Part 4) was rinsed with $CH_2Cl_2$ (20 ml), which was added to the reaction. The reaction was stirred at room temperature for 1 hour and poured into $H_2O$ (80 ml). The products were extracted with $CH_2Cl_2$ (40 ml×3). The combined $CH_2Cl_2$ layers were washed with $H_2O$ (20 ml×3) and dried over $MgSO_4$. Filtration and evaporation of solvent gave a straw colored liquid (10.8 g). This was distilled to give the title compound (8.4 g, 36.3 mmole, 67%, 41° C./0.015 mmHg) as a colorless liquid.

(6) 5-Bromo-2,2-difluoropentanoic acid

HBr gas was introduced into 48% HBr in $H_2O$ (100 ml) with occasional cooling in an ice bath until the weight became 180 g. The HBr solution was then added to Part 5) compound (8.4 g, 36.3 mmole) at room temperature and the reaction was stirred for 5 hours at room temperature. The reaction was cooled to 0° C. and poured into $Et_2O$ (900 ml) in an ice bath. The products were extracted into the $Et_2O$ layer. The water layer was further extracted with $Et_2O$ (200 ml and 100 ml). The combined ether layers were washed with $H_2O$ (200 ml). The $H_2O$ wash was backwashed with $Et_2O$ (100 ml). The $Et_2$ O layers were combined and dried over $MgSO_4$. Filtration and evaporation of solvent gave the title compound (7.8 g, quant.) as a colorless liquid.

(7)
(4-Carboxy-3,3-difluorobutyl)triphenylphosphonium bromide

Acetonitrile (23 ml) was added to a mixture of triphenylphosphine (6.7 g, 25.7 mmole) and Part (6) compound (4.6 g, 21.2 mmole). The solution was heated at gentle reflux under magnetic stirring for 30 hours. Toluene (46 ml) was then added and the reaction was brought to reflux for a brief period. The reaction was allowed to cool to 5° C. and kept overnight. The resulting white precipitates were collected, washed with cold acetonitrile/toluene (1/2), and dried in a heated vacuum oven (60° C. ~5 mmHg) to give the title bromide (9.8 g, 20.4 mmole, 96.5%) as white solid.

C.
[1S-[1β,2α(5Z),3α,4β]]-2,2-Difluoro-7-[3-[[[[(Butylamino)carbonyl]oxy]acetyl]amino]methyl]-7-oxabicyclo[2.2.1]hept-2-yl]-5-heptenoic acid (4-Carboxy-3,3-difluorobutyl)triphenylphosphonium bromide (1.27 g) (prepared in Part B) is suspended in THF (15 ml). KOt-Amylate (1.7M in toluene, 3 ml) is added at room temperature. The reaction is stirred for 4 hours. The resulting solution is transferred dropwise to aldehyde obtained in Part A, (177.1 mg) in THF (10 ml) at 0° C. The reaction is warmed to room temperature and stirred for 15 hours. Saturated $NH_4Cl$ (25 ml) is added and the products are extracted with EtOAc (40 ml×3). The combined organic layers are washed with brine (30 ml) and dried over $MgSO_4$. Filtration and evaporation of solvents afford a brown colored oil, which is purified by silica gel column to give the title compound.

EXAMPLE 4

[1S-[1β,2α(2E,5Z),3α,4β]]-7-[3-[[[[(Butylamino)carbonyl]oxy]acetyl]amino]methyl]-7-oxabicyclo[2.2.1]hept-2-yl]-2,5-heptadienoic acid (4-Carboxy-2-butenyl)triphenylphosphonium bromide (1.13 g) is suspended in THF (15 ml). KOt Amylate (1.7M in toluene, 3 ml) is added at room temperature. The reaction is stirred for 4 hours. The resulting solution is transferred dropwise to aldehyde obtained in Example 9 Part A, (177.1 mg) in THF (10 ml) at 0° C. The reaction is warmed to room temperature and stirred for 15 hours. Saturated $NH_4Cl$ (25 ml) is added and the products are extracted with EtOAc (40 ml×3). The combined organic layers are washed with brine (30 ml) and dried over $MgSO_4$. Filtration and evaporation of solvents afford a crude product, which is purified by silica gel column to give the title compound.

EXAMPLE 5

[1S-[1β,2α(5Z),3α,4β]]-2-Hydroxy-7-[3-[[[[(butylamino)carbonyl]oxy]acetyl]amino]methyl]7-oxabicyclo[2.2.1]hept-2-yl]-5-heptenoic acid, methyl ester Lithium diisopropylamine (LDA) is prepared in an argon atmosphere, by dissolving diisopropylamine (0.89 ml, 644 mg, 6.36 mmol) in THF (30 ml) at 0° C. and adding dropwise a solution of 2N-n-BuLi in hexane (2.55 ml, 5.1 mmol). After stirring at 0° C. for 30 minutes, the LDA solution was cooled at −78° C. Ester prepared in Example 1 (767 mg, 1.8 mmol) dissolved in THF (10 ml) is added to LDA at −78° C. The reaction is stirred at −78° C. for 1 hour. Oxodiperoxymolybdenum(pyridine)(hexamethylphosphoric triamide) (MoOPH) (2.76 g, 6.36 mmol) is added in one portion. The mixture is stirred at −78° C. for 30 minutes and at −30° C. to −40° C. for 1 hour. The reaction is quenched by adding saturated $NaHSO_3$ (20 ml), and allowed to warm to room temperature. After stirring at room temperature for 30 minutes, $H_2O$ (0 ml) is added to give two layers which are separated. The aqueous layer is extracted with EtOAc (100 ml×3). The combined organic layers are washed with 1N-HCl (50 ml×2), brine (20 ml×2) and dried over $MgSO_4$. Filtra-

EXAMPLE 6

[1S-[1β,2α(5Z),3α,4β]]-2-Hydroxy-7-[3-[[[[[(butylamino)carbonyl]oxy]acetyl]amino]methyl]-7-oxabicyclo[2.2.1]hept-2-yl]-5-heptenoic acid Following the procedure of Example 2 except substituting the Example 5 ester for the Example 1 ester, the title compound is obtained.

EXAMPLE 7

[1S-[1β,2α(5Z),3α,4β]]-7-[3-[[[[[(Butylamino)carbonyl]oxy]acetyl]amino]methyl]-7-oxabicyclo[2.2.1]hept-2-yl]-5-heptene-1,2-diol NaBH$_4$ (185 mg) is added to a magnetically stirred solution of hydroxy ester prepared in Example 11 (438 mg) at 0° C. After hydrogen evolution has subsided, the reaction is allowed to warm to room temperature and stirred overnight (16 hours). Saturated NH$_4$Cl (10 ml) is added and stirred for 1 hour. Most of MeOH is removed in vacuo and the residue is partitioned between EtOAc (50 ml) and brine (10 ml). The water layer is reextracted with EtOAc (40 ml×2). The combined organic layers are washed with brine (30 ml) and dried over MgSO$_4$. Filtration and evaporation of solvent give a crude product, which is purified by silica gel column. The title compound is thus obtained.

EXAMPLE 8

[1S-[1β,2α(5Z),3α,4β]]-N-Methyl-7-[3-[[[[[(butylamino)carbonyl]oxy]acetyl]amino]methyl]-7-oxabicyclo[2.2.1]hept-2-yl]-5-heptenamide 40% MeNH$_2$ in H$_2$O (2 ml) is added to a magnetically stirred solution of ester prepared in Example 1 (153 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 9

[1S-[1β,2α(5Z),3α(R),4β]]-7-[3-[[[[1-Oxo-2-[(butylamino)carbonyl]oxy]propyl]amino]methyl]-7-oxabicyclo[2.2.1]hept-2-yl]-5-heptenoic acid, methyl ester A. 2-[(Butylamino)carbonyl]oxy]propionic acid Following the procedure of Example 1 Part A except substituting 2(R)-hydroxypropionic acid, methyl ester for methyl glycolate, the title compound is obtained.

B.
[1S-[1β,2α(5Z),3α(R),4β]]-7-[3-[[[[1-Oxo-2-[(butylamino)carbonyl]oxy]propyl]amino]methyl]-7-oxabicyclo[2.2.1]hept-2-yl]-5-heptenoic acid, methyl ester Part A acid compound (1 mmol) and chiral amine prepared as described in Example 1 Part C (1 mmol) are coupled using CDI (1 mmol) as described in Example 1 Part D. The crude product is chromatographed on silica gel (Baker for flash chromatography) eluting with 2-4% MeOH in Et$_2$O. The eluted product is triturated with Et$_2$O to give the title methyl ester.

EXAMPLE 10

[1S-[1β,2α(5Z),3α(R),4β]]-7-[3-[[[[1-Oxo-2-[(butylamino)carbonyl]oxy]propyl]amino]methyl]-7-oxabicyclo[2.2.1]hept-2-yl]-5-heptenoic acid The Example 9 methyl ester (215 mg, 0.49 mmol) is hydrolyzed with LiOH solution in a THF-water mixture as described in Example 2. The viscous product is dissolved in EtOAc (~2-3 ml). On standing crystalline material is deposited. This is harvested by filtration and washed with Et$_2$O to give title acid.

EXAMPLE 11

[1S-[1β,2α(5Z),3α,4β]]-7-[3-[[[[2-Methyl-2-[(butylamino)carbonyl]oxy]-1-oxopropyl]amino]methyl]-7-oxabicyclo[2.2.1]hept-2-yl]-5-heptenoic acid, methyl ester A. 2-[(Butylamino)carbonyl]oxy]-2-methyl propionic acid Following the procedure of Example 1 Part A except substituting 2-hydroxy-2-methyl propionic acid, methyl ester for methyl glycolate, the title compound is obtained.

B.
[1S-[1β,2α(5Z),3α,4β]]-7-[3-[[[[2-Methyl-2-[(butylamino)carbonyl]oxy]1-oxopropyl]amino]methyl]-7-oxabicyclo[2.2.1]hept-2-yl]-5-heptenoic acid, methyl ester Part A compound (1 mmol) is reacted with CDI (1 mmol) and then with chiral amine prepared as described in Example 1 Part C (1 mmol) employing the method described in Example 1 Part D. The crude product is chromatographed on silica gel (25 g, Baker for flash chromatography), eluting with 2% MeOH in Et$_2$O to give title ester.

EXAMPLE 12

[1S-[1β,2α(5Z),3α,4β]]-7-[3-[[[[2-Methyl-2-[(butylamino)carbonyl]oxy]-1-oxopropyl]amino]methyl]-7-oxabicyclo[2.2.1]hept-2-yl]-5-heptenoic acid The Example 11 methyl ester (231 mg, 0.51 mmol) is hydrolyzed with LiOH in a water-THF mixture as described in Example 2. The product is crystallized from ethyl acetate (~4 ml) to give title acid.

EXAMPLE 13

[1S-[1β,2α(5Z),3α,4β]]-7-[3-[[[[[(Pentylamino)carbonyl]oxy]acetyl]amino]methyl]-7-oxabicyclo[2.2.1]hept-2-yl]-5-heptenoic acid, methyl ester A. [[(Pentylamino)carbonyl]oxy]acetic acid Following the procedure of Example 1 Part A except substituting pentyl isocyanate for n-butylisocyanate, the title compound is obtained.

B.
[1S-[1β,2α(5Z),3α,4β]]-7-[3-[[[[[(Pentylamino)carbonyl]oxy]acetyl]amino]methyl]-7-oxabicyclo[2.2.1]hept-2-yl]-5-heptenoic acid, methyl ester Part A compound (1 mmol) is reacted with CDI (1 mmol) and then with chiral amine (1 mmole) prepared as described in Example 1 Part C employing the method described in Example 1 Part D. The crude product is chromatographed on silica gel (25 g, Baker for flash chromatography) eluting with EtOAc and 2% MeOH in EtOAc to give title ester.

EXAMPLE 14

[1S-[1β,2α(5Z),3α,4β]]-7-[3-[[[[[(Pentylamino)carbonyl]oxy]acetyl]amino]methyl]-7-oxabicyclo-[2.2.1]hept-2-yl]-5-heptenoic acid The Example 13 methyl ester (257 mg, 0.607 mmol) is hydrolyzed with LiOH in a water-THF mixture as described in Example 2. The crude crystalline product is recrystallized from EtOAc (4 ml) to give title acid.

EXAMPLE 15

[1S-(1β,2α,3α,4β)]-7-[3-[[[[[(Butylamino)carbonyl]oxy]acetyl]amino]methyl]-7-oxabicyclo[2.2.1]hept-2-yl]heptanoic acid, methyl ester A. [1S-(1β,2α,3α,4β)]-7-[3-(Hydroxymethyl)-7-oxabicyclo[2.2.1]hept-2-yl]heptanoic acid, methyl ester To 800 mg (3.0 mmole) of the [1S-[1β,2α(Z),-3α,4β]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. [1S-(1β,2α,3α,4β)]-7-[3-[[[[[(Butylamino)carbonyl]oxy]acetyl]amino]methyl]-7-oxabicyclo[2.2.1]hept-2-yl]heptanoic acid, methyl ester Following the procedure of Example 1 except substituting the Part A alcohol-ester for the alcohol ester employing in Example 1 Part B, the title product is obtained.

EXAMPLE 16

[1S-[1β,2α(5Z),3α,4β]]-7-[3-[[[[1-Oxo-3-[(butylamino)-carbonyl]oxy]propyl]amino]methyl]-7-oxabicyclo[2.2.1]hept-2-yl]-5-heptenoic acid, methyl ester A. [3-[(Butylamino)carbonyl]oxy]propionic acid Following the procedure of Example 1 Part A except substituting 3-hydroxypropionic acid, methyl ester for methyl glycolate, the title compound is obtained.

B. [1S-[1β,2α(5Z),3α,4β]]-7-[3-[[[[1-Oxo-3-[(butylamino)-carbonyl]oxy]propyl]amino]methyl]-7-oxabicyclo[2.2.1]hept-2-yl]-5-heptenoic acid, methyl ester Part A acid (1 mmol) is reacted with carbonyl diimidazole (1 mmol) followed by [1S-[1β,2α(5Z)-,3α,4β]]-7-[3-(aminomethyl)-7-oxabicyclo[2.2.1]hept-2-yl]-5-heptenoic acid, methyl ester (prepared as described in Example 1 Part C (1 mmole)). The crude product is chromatographed on silica gel (25 g, Baker for flash chromatography) eluting with 5–10% MeOH in Et₂O to give title product.

EXAMPLE 17

[1S-[1β,2α(5Z),3α,4β]]-7-[3-[[[[1-Oxo-3-[(butylamino)-carbonyl]oxy]propyl]amino]methyl]-7-oxabicyclo[2.2.1]hept-2-yl]-5-heptenoic acid The Example 16 methyl ester (311 mg, 0.71 mmol) is hydrolyzed with LiOH in a THF—H₂O mixture as described in Example 2 to give a solid. This is recrystallized from EtOAc to give title acid.

EXAMPLE 18

[1S-[1β,2α(5Z),3α,4β]]-7-[3-[[[[[(4-Biphenylamino)carbonyl]oxy]acetyl]amino]methyl]-7-oxabicyclo[2.2.1-]hept-2-yl]-5-heptenoic acid, methyl ester A. [[(4-Biphenylamino)carbonyl]oxy]acetic acid Following the procedure of Example 1 Part A except substituting 4-biphenylisocyanate for n-butylisocyanate, the title compound is obtained.

B. [1S-[1β,2α(5Z),3α,4β]]-7-[3-[[[[[(4-Biphenylamino)carbonyl]oxy]acetyl]amino]methyl]-7-oxabicyclo[2.2.1-]hept-2-yl]-5-heptenoic acid, methyl ester Part A acid (1 mmol) is reacted with carbonyldiimidazole (1 mmole) followed by [1S-[1β,2α(5Z)-,3α,4β]]-7-[3-(aminomethyl)-7-oxabicyclo[2.2.1]hept-2-yl]-5-heptenoic acid, methyl ester (1 mmole) as in Example 1, Part C. After stirring overnight at room temperature. DMF (3 ml) is added and the mixture is left stirring an additional 24 hours. After the usual work up, the product is chromatographed on silica gel (30 g of Baker for flash chromatography), eluting with 2% MeOH in CH₂Cl₂. The material obtained from the column is crystallized from ethyl acetate (2 ml) to give title ester.

EXAMPLE 19

[1S-[1β,2α(5Z),3α,4β]]-7-[3-[[[[[(4-Biphenylamino)carbonyl]oxy]acetyl]amino]methyl]-7-oxabicyclo[2.2.1-]hept-2-yl]-5-heptenoic acid The Example 18 methyl ester (0.279 mmol) is hydrolyzed with LiOH as described in Example 2 to give a solid. This is triturated with EtOAc to give title acid.

EXAMPLE 20

[1S-(1β,2α,3α,4β)]-7-[3-[[[[2-Methyl-2-[(butylamino)-carbonyl]oxy]-1-oxopropyl]amino]methyl]-7-oxabicyclo[2.2.1]hept-2-yl]heptanoic acid Following the procedure of Example 2 except substituting the Example 11 Part A acid for the Example 1 Part A acid, the title acid is obtained.

EXAMPLE 21

[1S-[1β,2α(5Z),3α,4β]]-7-[3-[[[[[(Propylamino)carbonyl]oxy]acetyl]amino]methyl]-7-oxabicyclo[2.2.1-]hept-2-yl]-5-heptenoic acid Following the procedure of Examples 1 and 2 except substituting propylisocyanate for n-butyl isocyanate, the title compound is obtained.

EXAMPLE 22

[1S-[1β,2α(5Z),3α,4β]]-7-[3-[[[[[(Ethylamino)carbonyl]oxy]acetyl]amino]methyl]-7-oxabicyclo[2.2.1]hept-2-yl]-5-heptenoic acid Following the procedure of Examples 1 and 2 except substituting ethylisocyanate for n-butylisocyanate, the title compound is obtained.

EXAMPLE 23

[1S-[1β,2α(5Z),3α,4β]]-7-[3-[[[[(2-Butenylamino)carbonyl]oxy]acetyl]amino]methyl]-7-oxabicyclo[2.2.1-]hept-2-yl]-5-heptenoic acid Following the procedure of Examples 1 and 2 except substituting 2-butenylisocyanate for n-butylisocyanate, the title compound is obtained.

EXAMPLE 24

[1S-[1β,2α(5Z),3α,4β]]-7-[3-[[[[(3-Butynylamino)carbonyl]oxy]acetyl]amino]methyl]-7-oxabicyclo[2.2.1-]hept-2-yl]-5-heptenoic acid Following the procedure of Examples 1 and 2 except substituting 3-butynylisocyanate for n-butylisocyanate, the title compound is obtained.

EXAMPLE 25

[1S-[1β,2α(5Z),3α,4β]]-7-[3-[[[[(Phenylamino)carbonyl]oxy]acetyl]amino]methyl]-7-oxabicyclo[2.2.1-]hept-2-yl]-5-heptenoic acid Following the procedure of Examples 1 and 2 except substituting phenylisocyanate for n-butylisocyanate, the title compound is obtained.

EXAMPLE 26

[1S-(1β,2α,3α,4β)]-7-[3-[[[[[(Hexylamino)carbonyl]oxy]acetyl]amino]methyl]-7-oxabicyclo[2.2.1]hept-2-yl]heptanoic acid Following the procedure of Example 15 except substituting hexylisocyanate for n-butylisocyanate, the title compound is obtained.

EXAMPLE 27

[1S-(1β,2α,3α,4β)]-7-[3-[[[[[(2-Propenylamino)carbonyl]oxy]acetyl]amino]methyl]-7-oxabicyclo[2.2.1-]hept-2-yl]heptanoic acid Following the procedure of Example 15 except substituting 2-propenylisocyanate for n-butylisocyanate, the title compound is obtained.

EXAMPLE 28

[1S-(1β,2α,3α,4β)]-7-[3-[[[[[(4-Pentynylamino)carbonyl]oxy]acetyl]amino]methyl]-7-oxabicyclo[2.2.1-]hept-2-yl]heptanoic acid Following the procedure of Example 15 except substituting 4-pentynylisocyanate for n-butylisocyanate, the title compound is obtained.

EXAMPLE 29

[1S-[1β,2α(5Z),3α,4β]]-7-[3-[2-[[[[(Butylamino)carbonyl]oxy]acetyl]amino]ethyl]-7-oxabicyclo[2.2.1]hept-2-yl]-5-heptenoic acid

A.

[1S-[1β,2α(Z),3α,4β]]-7-[3-(2-Oxo)ethyl-7-oxabicyclo[2.2.1]hept-2-yl]-5-heptenoic acid, methyl ester Into a dry 100 ml round bottom 3-necked flash containing a stir bar was added dried 12.9 g (37.7 mmoles) methoxymethyltriphenylphosphonium chloride ((C₆H₅)₃P⁺—CH₂OCH₃Cl⁻) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml satured NH₄Cl, and extracted with ether (4×200 ml). The combined ether phases were washed with NaCl, saturated solution, and dried (MgSO₄) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1-]hept-2-yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1S-[1β,2α(5Z),3α,4β]]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH₄ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO₃, saturated NaCl and dried (MgSO₄). The ether is evaporated to yield the title B compound.

C.

[1S-[1β,2α(Z),3α,4β]]-7-[3-[2-[[[[(Butylamino)carbonyl]oxy]acetyl]amino]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 30

[1S-(1β,2α,3α,4β)]-7-[3-[2-[[[[(Butylamino)carbonyl]oxy]acetyl]amino]ethyl]-7-oxabicyclo[2.2.1]hept-2-yl]heptanoic acid Following the procedure of Examples 29 and 1 except substituting [1S-(1β,2α,3α,4β)]-7-[3-formyl-7-oxabicyclo[2.2.1]hept-2-yl]heptanoic acid, methyl ester for [1S-[1β,2α(Z),3α,4β]]-7-[3-formyl-7-oxabicyclo[2.2.1]hept-2-yl]-5-heptenoic acid, methyl ester, the title compound is obtained.

EXAMPLE 31

[1S-[1β,2α(5Z),3α,4β]]-7-[3-[2-[[[[(Heptylamino)carbonyl]oxy]acetyl]amino]ethyl]-7-oxabicyclo[2.2.1]hept-2-yl]-5-heptenoic acid Following the procedure of Example 29 except substituting heptylisocyanate for n-butylisocyanate, the title compound is obtained.

EXAMPLE 32

[1S-(1β,2α,3α,4β)]-7-[3-[2-[[[[(2-Butenylamino)carbonyl]oxy]acetyl]amino]ethyl]-7-oxabicyclo[2.2.1]hept-2-yl]heptanoic acid Following the procedure of Examples 29 and 15 except substituting 2-butenylisocyanate for n-butylisocyanate, the title compound is obtained.

EXAMPLE 33

[1S-[1β,2α(5Z),3α,4β]]-7-[3-[4-[[[[(Butylamino)carbonyl]oxy]acetyl]amino]butyl]-7-oxabicyclo[2.2.1]hept-2-yl]-5-heptenoic acid

A.
[1S-[1β,2α(5Z),3α,4β]]-7-[3-(3-Oxo)propyl-7-oxabicyclo[2.2.1]hept-2-yl]-5-heptenoic acid, methyl ester Following the procedure of Example 29 Part A except substituting [1S-[1β,2α(Z),3α,4β]]-7-[3-(2-oxo)ethyl-7-oxabicyclo[2.2.1]hept-2-yl]-5-heptenoic acid, methyl ester for [1S-[1β,2α(Z),3α,4β]]-7-[3-formyl-7-oxabicyclo[2.2.1]hept-2-yl]-5-heptenoic acid, methyl ester, the title A compound is obtained.

B.
[1S-[1β,2α(Z),3α,4β]]-7-[3-(4-Oxo)butyl-7-oxabicyclo[2.2.1]hept-2-yl]-5-heptenoic acid, methyl ester Following the procedure of Example 29 Part A except substituting the aldehyde from Part A above for [1S-[1β,2α(Z),3α,4β]]-7-[3-formyl-7-oxabicyclo[2.2.1]hept-2-yl]-5-heptenoic acid, methyl ester, the title B compound is obtained.

C.
[1S-[1β,2α(Z),3α,4β]]-7-[3-(4-Hydroxybutyl)-7-oxabicyclo[2.2.1]hept-2-yl]-5-heptenoic acid, methyl ester Following the procedure of Example 29 Part B except substituting the title B aldehyde for [1S-[1β,2α(Z),3α,4β]]-7-[3-(2-oxo)ethyl-7-oxabicyclo[2.2.1]hept-2-yl]-5-heptenoic acid, methyl ester, the title C alcohol is obtained.

D.
[1S-[1β,2α(Z),3α,4β]]-7-[3-[4-[[[[(Butylamino)carbonyl]oxy]acetyl]amino]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 34

[1S-[1β,2α(5Z),3α,4β]]-8-[3-[[[[(Butylamino)carbonyl]oxy]acetyl]amino]methyl]-7-oxabicyclo[2.2.1]hept-2-yl]-5-octenoic acid

A.
[1S-(1β,2α,3α,4β)]-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XIII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO4 and concentrated in vacuo. The solid residue was triturated with hexane (1 liter), filtered, and dried in vacuo to yield 220 g (100%) of desired compound (hemiacetal F in reaction sequence C), m.p. 104°–105° C., $[\alpha]_D = +27°$ c=1 MeOH.

TLC: Silica gel; EtOAc; $R_f=0.3$; Ce(SO4)2.

The above Wittig procedure was repeated on the hemiacetal F used in place of hemiacetal XIII to form the title aldehyde.

B.
[1S-[1β,2α(Z),3α,4β]]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.15 g (6.25 mmol) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane (CH$_2$N$_2$) in Et$_2$O to give the title compound.

C. [1S-[1β,2α(Z),3α,4β]]-8-[3-[[[[[(Butylamino)carbonyl]oxy]acetyl]amino]methyl]-7-oxabicyclo[2.2.1]hept-2-yl]-5-octenoic acid Following the procedure of Examples 1 and 2 except substituting the title B ester for the ester used in Example 1 Part B, the title compound is obtained.

EXAMPLE 35

[1S-[1β,2α(Z),3α,4β]]-6-[3-[[[[[(Butylamino)carbonyl]oxy]acetyl]amino]methyl]-7-oxabicyclo[2.2.1]hept-2-yl]-1-(1H-tetrazol-5-yl)-4-hexene

A.
[1S-[1β,2α(5Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluant to provide 2 g of title A compound.

B.
[1S-[1β,2α(5Z),3α,4β]]-6-[3-[[[[[(Butylamino)carbonyl]oxy]acetyl]amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part B, the title compound is obtained.

EXAMPLE 36

[1S-[1β,2α(5Z),3α,4β]]-7-[3-[[[[[(Butylamino)carbonyl]oxy]acetyl]amino]methyl]-7-oxabicyclo[2.2.1]hept-2-yl]-N-hydroxy-N-methyl-5-heptenamide A solution of Example 2 acid (0.82 mmole) in dry tetrahydrofuran (5.0 ml) is treated with carbonyldiimidazole (CDI) (0.82 mmole) at 0° C. and stirred at 0° for 1 hour and at room temperature for 1 hour. The reaction is added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml). The mixture is stirred at 0° under nitrogen for 30 minutes and at room temperature overnight, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 37

[1S-[1β,2α(6Z),3α,4β]]-7-[3-[[[[[(Butylamino)carbonyl]oxy]acetyl]amino]methyl]-7-oxabicyclo[2.2.1]hept-2-yl]-6-heptenoic acid

A.
[1S-[1β,2α(6Z),3α,4β]]-7-[3-(Hydroxymethyl)-7-oxabicyclo[2.2.1]hept-2-yl]-heptenoic acid, methyl ester A slurry of carboxypentyl triphenylphosphonium bromide in THF is cooled in an ice bath and treated dropwise with 1.4M KOt-amylate in toluene. After completion of this addition, the reaction mixture is allowed to warm to room temperature and is stirred for 6 hours. To this stirred solution is then added a solution of hemiacetal XII (reaction sequence G) (prepared as described in Example 3 of U.S. Pat. No. 4,143,054) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO$_3$ solution. The aqueous extracts are acidified to pH~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title ester.

B.
[1S-[1β,2α(6Z),3α,4β]]-7-[3-[[[[[(Butylamino)carbonyl]oxy]acetyl]amino]methyl]-7-oxabicyclo[2.2.1]hept-2-yl]-6-heptenoic acid Following the procedure of Example 1 except substituting the Part A ester for the hydroxymethyl compound used in Example 1 Part B, the title compound is obtained.

EXAMPLE 38

[1S-[1β,2α(2E),3α,4β]]-7-[3-[[[[[(Butylamino)carbonyl]oxy]acetyl]amino]methyl]-7-oxabicyclo[2.2.1]hept-2-yl]2-heptenoic acid

A.
[1S-(1β,2α,3α,4β)]-5-[3-(Hydroxymethyl)-7-oxabicyclo[2.2.1]hept-2-yl]pentanal Following the procedure of Example 37 Part A, except substituting [1S-(1β,2α,3α,4β)]-3-[3-(hydroxymethyl)-7-oxabicyclo[2.2.1]hept-2-yl]propionaldehyde for the hemiacetal XIII (see reaction sequence G or H), [1S-(1β,2α,3α,4β)]-4-[3-(hydroxymethyl)-7-oxabicyclo[2.2.1]hept-2-yl]butanal is obtained. Then by repeating the procedure of Example 47 Part A on [1S-(1β,2α,3α,-4β)]-4-[3-(hydroxymethyl)-7-oxabicyclo[2.2.1]hept-2-yl]butanal, the title A aldehyde is produced.

B. [1S-[1β,2α(2E),3α,4β]]-7-[3-(Hydroxymethyl)-7-oxabicyclo[2.2.1]hept-2-yl]-2-heptenoic acid, methyl ester To a stirred solution of the title A aldehyde in benzene is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C. [1S-[1β,2α(2E),3α,4β]]-7-[3-[[[[(Butylamino)carbonyl]oxy]acetyl]amino]methyl]-7-oxabicyclo[2.2.1]hept-2-yl]-2-heptenoic acid Following the procedure of Example 1 except substituting the Part B ester for the ester used in Example 1 Part B, the title compound is obtained.

EXAMPLE 39

[1S-[1β,2α(5Z),3α,4β]]-7-[3-[(Methylamino)methyl]-7-oxabicyclo[2.2.1]hept-2-yl]-5-heptenoic acid, methyl ester Chiral amine from Example 1, Part C, (1 mmole) and N,N-dimethylformamide dimethylacetal (1.5 mmole) are dissolved in CH$_2$Cl$_2$ (6 ml). The reaction is stirred at room temperature overnight. The solvent and the excess reagent are evaporated to give crude amidine, which is dissolved in CH$_2$Cl$_2$ (5 ml). Methyl triflate (2 mmole) is added into the reaction at room temperature and the reaction is stirred for 1 hour at room temperature. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated NaHCO$_3$. The water layer is extracted with ethyl ether, which is dried over MgSO$_4$. Filtration and evaporation of the solvent leave a crude product, which is purified by silica gel column to give the title compound.

The title compound is then employed in place of the chiral amine from Example 1 Part C to prepare compounds of the invention wherein R$^1$ is CH$_3$.

EXAMPLES 40 TO 67

Following the procedures outlined in the specification and described in the above working Examples, the following compounds may be prepared.

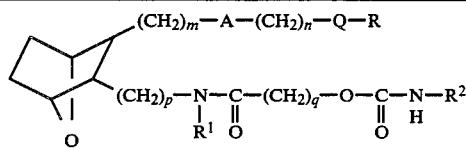

| Ex. No. | m | A | (CH$_2$)$_n$ | Q | R | p | R$^1$ | (CH$_2$)$_q$ | R$^2$ |
|---|---|---|---|---|---|---|---|---|---|
| 40. | 2 | CH=CH | CH$_2$ | CH=CH | CO$_2$H | 1 | H | (CH$_2$)$_2$ | H |
| 41. | 3 | (CH$_2$)$_2$ | (CH$_2$)$_2$ | CH$_2$ | CH$_2$OH | 2 | C$_2$H$_5$ | (CH$_2$)$_3$ | CH$_3$ |
| 42. | 4 | CH=CH | (CH$_2$)$_3$ | —CH(OH)— | tetrazol-5-yl | 3 | H | (CH$_2$)$_4$ | —CH=CH—CH$_3$ |
| 43. | 1 | (CH$_2$)$_2$ | (CH$_2$)$_4$ | —CH(F)— | CN(CH$_3$)C$_2$H$_5$ (C=O) | 1 | CH$_3$ | (CH$_2$)$_5$ | —C≡C—CH$_3$ |
| 44. | 0 | CH=CH | (CH$_2$)$_5$ | —CF$_2$— | CN—OH(C=O), CH$_3$ | 2 | H | (CH$_2$)$_6$ | —CH$_2$—C≡C—CH$_3$ |
| 45. | 2 | CH=CH | —CH(CH$_3$)— | CH=CH | CN—OCH$_3$ (C=O), H | 3 | C$_2$H$_5$ | (CH$_2$)$_7$ | —CH$_2$—C=C—CH$_3$ (H,H) |
| 46. | 3 | (CH$_2$)$_2$ | —C(CH$_3$)$_2$— | CH$_2$ | CN—OC$_2$H$_5$ (C=O), CH$_3$ | 4 | H | —CH(CH$_3$)— | C$_6$H$_5$ |
| 47. | 4 | (CH$_2$)$_2$ | (CH$_2$)$_4$ | —CH(OH)— | CNHC$_6$H$_5$ (C=O) | 1 | C$_3$H$_7$ | —CH$_2$— | C$_6$H$_5$ |

-continued

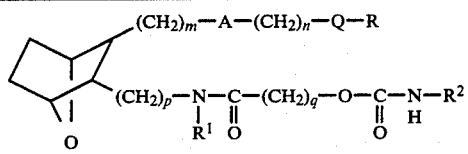

| Ex. No. | m | A | (CH₂)ₙ | Q | R | p | R¹ | (CH₂)q | R² |
|---|---|---|---|---|---|---|---|---|---|
| 48. | 1 | CH=CH | −C(CH₃)(CH₃)−CH₂− | −CHF− | CO₂Li | 2 | H | −CH₂−CH(CH₃)− | CH₂C₆H₅ |
| 49. | 0 | CH=CH | −CH(CH₃)CH(CH₃)− | −CF₂− | CO₂Na | 3 | CH₃ | −CH₂−C(CH₃)(CH₃)− | −(CH₂)₂C₆H₅ |
| 50. | 1 | (CH₂)₂ | −C(CH₃)(F)−CH₂− | CH=CH | CO₂ glucamine salt | 4 | C₂H₅ | −CH₂−CH(CH₃)−CH₂− | −C₆H₄−p-CH₃ |
| 51. | 2 | CH=CH | −CHF−CHF− | CH₂ | CO₂ tris salt | 1 | H | −(CH₂)₃− | −C₆H₄−p-OH |
| 52. | 3 | (CH₂)₂ | −CF₂−CH₂− | −CH(OH)− | CH₂OH | 2 | C₄H₉ | −CH₂−CH(C₂H₅)− | −CH₃ |
| 53. | 4 | (CH₂)₂ | −(CH₂)₅− | −CHF− | tetrazole (N=N / N-NH) | 3 | H | −CH₂−CH(CH₃)−CH₂− | −C₂H₅ |
| 54. | 0 | CH=CH | −CH₂−CH(CH₃)−CH₂− | −CF₂− | O=CNH₂ | 4 | CH₂ | −C(CH₃)(CH₃)−CH₂− | −C₆H₅ |
| 55. | 0 | (CH₂)₂ | −CH₂−C(CH₃)(CH₃)− | — | O=CNHOH | 1 | C₂H₅ | (CH₂)₂ | −(CH₂)₃−C₆H₅ |
| 56. | 1 | CH=CH | CH₂ | — | O=CN(CH₃)₂ | 2 | C₂H₅ | −CH₂− | C₆H₁₃ |
| 57. | 2 | (CH₂)₂ | (CH₂)₂ | CH₂ | O=CN(CH₃)(OH) | 3 | CH₃ | −CH₂−C(CH₃)(CH₃)− | C₅H₁₁ |
| 58. | 3 | CH=CH | (CH₂)₃ | — | CO₂H | 4 | C₂H₅ | −CH₂−CH(CH₃)−CH(CH₃)−CH₂− | −(CH₂)₂−C₆H₅ |
| 59. | 4 | (CH₂)₂ | (CH₂)₄ | CH=CH | CH₂OH | 1 | C₃H₇ | (CH₂)₂ | −(CH₂)₄−C₆H₅ |
| 60. | 0 | CH=CH | −CH₂C(F)(F)− | CH₂ | tetrazole (N=N / N-NH) | 2 | C₄H₉ | (CH₂)₃ | H |
| 61. | 1 | (CH₂)₂ | −CH₂−C(CH₃)(CH₃)− | −CH(OH)− | O=CN(C₂H₅)₂ | 3 | C₅H₁₁ | −CHF−CH₂− | C₄H₉ |
| 62. | 2 | CH=CH | (CH₂)₅ | −CHF− | O=CNHC₆H₅ | 4 | H | −CF₂−CH₂− | −(CH₂)₂CH=CHCH₃ |

-continued

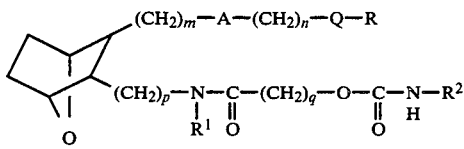

| Ex. No. | m | A | (CH₂)ₙ | Q | R | p | R¹ | (CH₂)_q | R² |
|---|---|---|---|---|---|---|---|---|---|
| 63. | 3 | (CH₂)₂ | $\overset{CH_3}{\underset{}{-CH_2-}}\overset{F}{\underset{}{CH-}}$ | $\overset{F}{\underset{}{-}}\overset{F}{\underset{}{C-}}$ | CH₂OH | 1 | H | (CH₂)₂ | C₆H₅ |
| 64. | 4 | (CH₂)₂ | (CH₂)₂ | CH=CH | 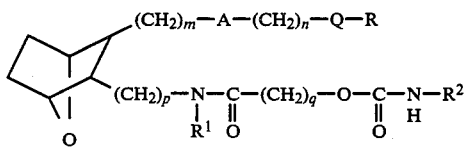 | 2 | H | CH₂ | —CH₂C₆H₅ |
| 65. | 0 | CH=CH | (CH₂)₃ | $\overset{OH}{\underset{}{-CH-}}$ | CO₂CH₃ | 3 | CH₃ | (CH₂)₃ | —C₆H₄-p-(CH₂)₇—CH₃ |
| 66. | 2 | (CH₂)₂ | (CH₂)₄ | CH₂ | CO₂CH₃ | 4 | CH₃ | (CH₂)₈ | C₆H₅ |
| 67. | 3 | CH=CH | (CH₂)₅ | — | CO₂H | 1 | CH₃ | (CH₂)₁₀ | C₆H₄p-CH₂CH₃ |

What is claimed is:

1. A compound having the structure

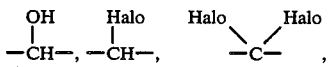

including all stereoisomers thereof, wherein m is 0 to 4; A is —CH=CH— or —CH₂—CH₂—; n is 1 to 5; Q is —CH=CH—, —CH₂—, $\overset{OH}{\underset{}{-CH-}}$, $\overset{Halo}{\underset{}{-CH-}}$, $\overset{Halo}{\underset{}{-}}\overset{Halo}{\underset{}{C-}}$, or a single bond; R is CO₂H, CO₂alkyl, CO₂ alkali metal, CO₂ polyhydroxyamine salt, —CH₂OH,

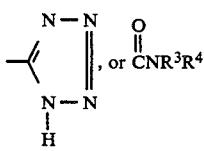, or $\overset{O}{\underset{}{\overset{\|}{CNR^3R^4}}}$ wherein R³ and R⁴ are the same or different and are H, lower alkyl, hydroxy, lower alkoxy or aryl at least one of R³ and R⁴ being other than hydroxy and lower alkoxy; p is 1 to 5; R¹ is H or lower alkyl; q is 1 to 12; and R² is H, lower alkyl, lower alkenyl containing 2 to 12 carbons, lower alkynyl containing 2 to 12 carbon atoms, aryl or arylalkyl, wherein lower alkyl or alkyl alone or as part of another group contains 1 to 12 carbon atoms and is unsubstituted or is substituted with halo, CF₃, alkoxy, aryl, alkyl-aryl, haloaryl, cycloalkyl, alkylcycloalkyl, hydroxy, alkylamino, alkanoylamino, arylcarbonylamino, nitro, cyano, thiol, or alkylthio;

aryl alone or as part of aiother group contains 6 to 10 carbon atoms in the ring portion and is unsubstituted or is substituted with 1 or 2 lower alkyl groups, 1 or 2 halogens, 1 or 2 hydroxy groups, 1 or 2 lower alkoxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups, and;

cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein R² is alkyl.

3. The compound as defined in claim 1 wherein A is CH=CH.

4. The compound as defined in claim 1 wherein m is 1 and n is 1 to 4.

5. The compound as defined in claim 1 wherein p is 1 and q is 1.

6. The compound as defined in claim 1 wherein Q is a single bond or CH₂.

7. The compound as defined in claim 1 wherein R is CO₂ alkyl or CO₂H.

8. The compound as defined in claim 1 wherein R¹ is H and R² is H or CH₃.

9. The compound as defined in claim 1 wherein m is 1, n is 2 to 4, Q is CH₂, a single bond, CH=CH, $\overset{OH}{\underset{}{-CH-}}$ or $\overset{halo}{\underset{}{-}}\overset{halo}{\underset{}{C-}}$, R is CO₂alkyl, CO₂H, CH₂OH, or $\overset{O}{\underset{}{\overset{\|}{CNR^3R^4}}}$, p is 1, R¹ is H, q is 1, and R² is alkyl or alkoxy.

10. The compound as defined in claim 1 having the name [1S-[1β,2α(5Z),3α,4β]]-7-[3-[[[[[(butylamino)carbonyl]oxy]amino]acetyl]amino]methyl]-7-oxabicyclo[2.2.1]hept-2-yl]-5-heptenoic acid or esters thereof, including all stereoisomers thereof.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 0.1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

16. A method of treating peripheral vascular diseases, which comprises topically or systemically administering to a mammalian host an effective amount of a compound as defined in claim 1 or a pharmaceutically acceptable salt thereof.

* * * * *